(12) United States Patent
Yam et al.

(10) Patent No.: US 8,372,977 B2
(45) Date of Patent: Feb. 12, 2013

(54) LUMINESCENT GOLD(III) COMPOUNDS CONTAINING BIDENTATE LIGAND FOR ORGANIC LIGHT-EMITTING DEVICES AND THEIR PREPARATION

(75) Inventors: Vivian Wing-Wah Yam, Hong Kong (CN); Vonika Ka-Man Au, Hong Kong (CN); Mei-Yee Chan, Hong Kong (CN); Keith Man-Chung Wong, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 261 days.

(21) Appl. No.: 12/822,812

(22) Filed: Jun. 24, 2010

(65) Prior Publication Data
US 2011/0012093 A1 Jan. 20, 2011

Related U.S. Application Data

(60) Provisional application No. 61/225,333, filed on Jul. 14, 2009.

(51) Int. Cl.
C07F 1/12 (2006.01)
H01L 51/50 (2006.01)
(52) U.S. Cl. ............... 546/2; 313/504; 428/690; 546/10
(58) Field of Classification Search ................ 546/2, 10; 428/690; 313/504
See application file for complete search history.

(56) References Cited

FOREIGN PATENT DOCUMENTS
WO WO 2007/088768 A1 * 8/2007

OTHER PUBLICATIONS

Adachi, C. et al. (2001). Endothermic energy transfer: A mechanism for generating very efficient high-energy phosphorescent emission in organic materials. *Applied Physics Letters*, 79(13): 2082-2084.
Adamovich, V. et al. (2002). High efficiency single dopant white electrophosphorescent light emitting diodes. *New Journal of Chemistry Articles*, 26: 1171-1178.
Baldo, M. A. et al. (1999). Very high-efficiency green organic light-emitting devices based on electrophosphorescence. *Applied Physics Letters*, 75(1): 4-6.
Baldo, M. A. et al. (1998). Highly efficient phosphorescent emission from organic electroluminescent devices. *Nature*, 395: 151-154.
Baldo, M. A. et al. (1999). Phosphorescent materials for application to organic light emitting devices. *Pure and Applied Chemistry*, 71(11): 2095-2106.
Braun, D. & Heeger, A. J. (1991). Visible light emission from semiconducting polymer diodes. *Applied Physics Letters*, 58(18): 1982-1984.
Burroughes, J. H. et al. (1990). Light-emitting diodes based on conjugated polymers. *Nature*, 347: 539-541.
Burrows, P. E. et al. (1997). Prospects and applications for organic light-emitting devices. *Current Opinion in Solid State and Materials Science*, 2(2): 236-243.
Cinellu, M. A. et al. (2000). Gold(III) derivatives with anionic oxygen ligands: Mononuclear hydroxo, alkoxo and acetato complexes. Crystal structure of [Au(bpy)(0Me)$_2$][PF$_6$]. *Journal of the Chemical Society, Dalton Trans.*: 1261-1265.

Cinellu, M. A. et al. (1999). Replacement of the chloride ligand in [Au(C,N,N)Cl][PF$_6$] cyclometallated complexes by C, N, O and S donor anionic ligands. *Journal of the Chemical Society, Dalton Trans.*: 2823-2831.
Helfrich, W. & Schneider, W. G. (1965). Recombination radiation in anthracene crystals. *Physical Review Letters*, 14(7): 229-231.
Kaneto, K. et al. (1974). Electroluminescence in polyethylene terephthalate. *Japanese Journal of Applied Physics*, 13(6): 1023-1024.
Kawamura, Y. et al. (2005). 100% phosphorescence quantum efficiency of Ir(III) complexes in organic semiconductor films. *Applied Physics Letters*, 86(7): 071104-1-071104-3.
O'Brien, D. F. & Baldo, M. A. (1999). Improved energy transfer in electrophosphorescent devices. *Applied Physics Letters*, 74(3): 442-444.
Rausch, A. F. et al. (2009). Matrix effects on the triplet state of the OLED emitter Ir(4,6-dFppy)$_2$(pic) (FIrpic): Investigations by high-resolution optical spectroscopy. *Inorganic Chemistry*, 48(5):1928-1937.
Tang, C. W. & Vanslyke, S. A. (1987). Organic electroluminescent diodes. *Applied Physics Letters*, 51(12): 913-915.
Welter, S. et al. (2003). Electroluminescent device with reversible switching between red and green emission. *Nature*, 421: 54-57.
Wong, K. M.-C. et al. (2007). A class of luminescent cyclometalated alkynylgold(III) complexes: Synthesis, characterization, and electrochemical, photophysical, and computational studies of [Au(CNC)(C#CR)] (CNC=[ ] C,N,C Bis-cyclometalated 2,6-Diphenylpyridyl). *Journal of the American Chemical Society*, 129(14): 4350-4365.
Wong, K. M.-C. et al. (2005). A novel class of phosphorescent gold(III) alkynyl-based organic light-emitting devices with tunable colour. *Chemical Communications*: 2906-2908.
Yam, V. W.-W. et al. (1993). Syntheses, crystal structures and photophysics of organogold (III) diimine complexes. *Journal of the Chemical Society, Dalton Trans.*: 1001-1002.
Yam, V. W.-W. et al. (2005). Luminescent gold(III) alkynyl complexes: Synthesis, structural characterization, and luminescence properties. *Angewandte Chemie International Edition*, 44: 3107-3110.

* cited by examiner

Primary Examiner — Charanjit Aulakh
(74) Attorney, Agent, or Firm — Saliwanchik, Lloyd & Eisenschenk

(57) ABSTRACT

Embodiments of the invention are directed to luminescent gold(III) compounds contains a bidentate ligand with at least one strong σ-donating group, a method of preparation of these compounds and the use of these compounds in organic light emitting devices. The gold(III) compounds have the chemical structure:

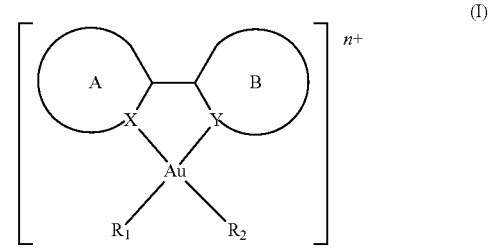

wherein: X is a nitrogen atom; Y is selected from a carbon or a nitrogen atom; A-B is a substituted or unsubstituted cyclometalating ligand (for Y=C) or diimine ligand (for Y=N); where A and B are cyclic structure derivatives; $R_1$ and $R_2$ are optionally substituted carbon donor ligands attached to the gold atom, with the proviso that $R_1$ and $R_2$ are not $-CH_3$, $-CH_2SiMe_3$, mesityl, pentafluorophenyl, $-CH_2C(O)R'$, $-CH(R)SO_2CH(R)-$, $-C_6H_4N=NC_6H_5$, and wherein $R_1$ and $R_2$ can optionally be combined into a bidentate ligand; and n is greater or equal to zero.

16 Claims, 4 Drawing Sheets

LUMINESCENT GOLD(III) COMPOUNDS CONTAINING BIDENTATE LIGAND FOR ORGANIC LIGHT-EMITTING DEVICES AND THEIR PREPARATION

CROSS-REFERENCE TO RELATED APPLICATION

The subject application claims the benefit of U.S. Provisional Application Ser. No. 61/225,333, filed Jul. 14, 2009, which is incorporated herein by reference in its entirety.

FIELD OF THE INVENTION

Embodiments of the invention are directed to a novel class of gold(III) compounds containing a bidentate ligand with two strong σ-donating groups and the syntheses of these compounds. These compounds can be used as light-emitting material in phosphorescence-based organic light-emitting devices (OLEDs).

BACKGROUND OF THE INVENTION

In recent years, much attention has been drawn towards the research and development of organic light-emitting devices. Such enormous increase in research interest is highly correlated to the potential application of OLEDs in commercial flat panel displays. With the advantages of low cost, light weight, low operating voltage, high brightness, robustness, color tunability, wide viewing angle, ease of fabrication onto flexible substrates as well as low energy consumption, OLEDs are considered as remarkably attractive candidates for flat panel display technologies.

Typically an OLED contains several layers of semiconductor sandwiched between two electrodes. The cathode is composed of a low work function metal alloy deposited by vacuum evaporation, whereas the anode is a transparent conductor such as indium tin oxide (ITO). Upon application of a DC voltage, holes injected by the ITO electrode and electrons injected by the metal electrode recombine to form excitons. Subsequent relaxation of excitons results in the generation of electroluminescence (EL).

In order to achieve higher OLED performance, multiple organic semiconductor layers can be incorporated that further separate the two electrodes. There are two main categories of materials that are used as these semiconductor layers, namely vacuum-deposited small molecules and spin-coated polymeric materials. Both fabrication methods have their respective advantages. Vacuum deposition generally allows better control over layer thickness and uniformity, while spin coating generally offers less complex fabrication having lower production cost [Burrows, P. E.; Forrest, S. R.; Thompson, M. E. *Current Opinion in Solid State and Materials Science*, 236 (1997)].

In spite of the fact that electroluminescence from organic polymers was initially reported in the 1970s [Kaneto, K.; Yoshino, K.; Koa, K.; Inuishi, Y. *Jpn. J. Appl. Phys.* 18, 1023 (1974)], it was only after the report on yellow-green electroluminescence from poly(p-phenylenenvinylene) (PPV) that light-emitting polymers and OLEDs received much attention [Burroughs, J. H.; Bradley, D. D. C.; Brown, A. R.; Marks, N.; Friend, R. H.; Burn, P. L.; Holmes, A. B. *Nature* 347, 539 (1990)]. Subsequently, similar studies reported PPV derivatives as light-emitting polymers [Braun, D.; Heeger, A. J. *Appl. Phys. Lett.* 58, 1982 (1991)]. Since then a number of new electroluminescent polymers have been investigated for improved properties.

Electroluminescence of organic materials was discovered in anthracene crystals immersed in liquid electrolyte in 1965 [Helfruch, W.; Schneider, W. G. *Phys. Rev. Lett.* 14, 229 (1965)]. Although lower operating voltages can be achieved by using a thin film of anthracene with solid electrodes, very low efficiency have been encountered for these single-layer devices. High-performance green electroluminescence from an organic small molecule, tris-(8-hydroxyquinoline) aluminum ($Alq_3$), was first reported in 1987 [Tang, C. W.; VanSlyke, S. A. *Appl. Phys. Lett.* 51, 913 (1987)]. A double-layer OLED with high efficiency and low operating voltage was described where $Alq_3$ was utilized both as emitting layer and electron transporting layer. Subsequent modification of the device to have a triple-layer structure gives better performance with higher efficiency.

Superior performance of phosphorescence-based OLEDs occurs when the semiconducting materials have short lifetimes. Short lifetimes can be achieved by mixing singlet and triplet excited states and exploiting spin-orbit (L-S) coupling. In the presence of a heavy metal center, the propensity of spin-orbit coupling can be greatly enhanced. Hence, the use of heavy metal complexes in OLEDs is generally advantageous relative to the use of purely organic materials. The lowest energy excited state of an organometallic compound is commonly a metal-to-ligand charge transfer (MLCT) triplet state, which can mix with the excited singlet state through L-S coupling, to result in higher photoluminescence efficiencies [Baldo, M. A.; Thompson, M. E.; Forrest, S. R. *Pure Appl. Chem.* 71, 2095 (1999)]. In 1998, Baldo et al. demonstrated a phosphorescence electroluminescent device with high quantum efficiency by using platinum(II) 2,3,7,8,12,13,17,18-octaethyl-21H,23H-porphine (PtOEP) as a dye [Baldo, M. A.; O'Brien, D. F.; You, Y.; Shoustikow, A.; Sibley, S.; Thompson, M. E.; Forrest, S. R. *Nature* 395, 151 (1998); O'Brien, D. F.; Baldo, M. A.; Thompson, M. E.; Forrest, S. R. *Appl. Phys. Lett.* 74, 442 (1999)]. A multilayer device where the emitting layer of $Alq_3$ is doped with PtOEP shows a strong emission at 650 nm that is attributed to the triplet excitons of PtOEP.

Cyclometalated iridium(III) is another class of materials used for high efficiency OLEDs, which is known to show intense phosphorescence. Baldo et al. reported the use of fac-tri(2-phenylpyridine)iridium(III) [$Ir(ppy)_3$] as phosphorescent emitting material as a dopant in a 4,4'-N,N'-diarbazole-biphenyl (CBP) host to give high quantum efficiency OLED [Baldo, M. A.; Lamansky, S.; Burrows, P. E.; Thompson, M. E.; Forrest, S. R. *Appl. Phys. Lett.* 75, 4 (1999)]. In light of the rich photoluminescence properties of $Ir(ppy)_3$, there has also been a growing interest in the incorporation of 2-phenylpyridine derivatives into iridium(III) center to prepare triplet emitters for OLED applications. Another example of triplet emitters is the sky-blue complex iridium(III) bis[2-(4',6'-difluorophenyl)pyridinato-N,$C^{2'}$]-picolinate [Ir(4,6-dFppy)$_2$(pic)], which exhibits a very high photoluminescence quantum yield of about 60% in solution and nearly 100% in a solid film when doped into high triplet energy host [Rausch, A. F.; Thompson, M. E.; Yersin, H. *Inorg. Chem.* 48, 1928 (2009); Adachi, C.; Kwong, R. C.; Djurovich, P. I.; Adamovich, V.; Baldo, M. A.; Thompson, M. E.; Forrest, S. R. *Appl. Phys. Lett.* 79, 2082 (2001); Kawamura, Y.; Goushi, K.; Brooks, J.; Brown, J. J.; Sasabe, H.; Adachi, C. *Appl. Phys. Lett.* 86, 071104 (2005)]. In spite of the extensive use of 2-phenylpyrdine and its derivatives in iridium(III) systems for the fabrication of OLEDs, the use of phosphors containing alternative metal centers with these ligands remains essentially unexplored and remains underdeveloped.

In addition to enhancing emission efficiencies, the ability to vary the emission color is desirable. Most approaches to color variance involve the use of different emission characteristics for color tuning. Examples that employ a single light-emitting material as dopant to generate more than one emission color are rare. Recent studies have shown that different emission colors from a single emissive dopant can be generated by using a phosphorescent material, by changing the bias direction or by changing the dopant concentration. Welter et al. reports the fabrication of a simple OLED consisting of semiconducting polymer PPV and phosphorescent ruthenium polypyridine dopant [Welter, S.; Krunner, K.; Hofstraat, J. W.; De Cola, D. *Nature*, 421, 54 (2003)]. At forward bias, red emission from the excited state of the phosphorescent ruthenium polypyridine dopant is observed, while the OLED emits a green emission at reverse bias where the lowest excited singlet state of PPV is populated. Adamovich et al. reports the use of a series of phosphorescent platinum(II) [2-(4,6-difluorophenyl)pyridinato-N,C$^{2'}$]-β-diketones as single emissive dopants in OLED [Adamovich, V.; Brooks, J.; Tamayo, A.; Alexander, A. M.; Djurovich, P. R.; D'Andrade, B. W.; Adachi, C.; Forrest, S. R.; Thompson, M. E. *New J. Chem.* 26, 1171 (2002)]. Both blue emission from monomeric species and orange emission from the aggregates are observed in such OLED where the relative intensity of the orange emission increases as the doping level increases. As a result, the electroluminescence color can be tuned by changing the dopant concentration with equal intensities to the monomeric and aggregate bands. In both cases, the change of electroluminescence color in an OLED can be accomplished by varying the external stimulus or fabrication conditions while employing the same light-emitting material.

Even though there has been increasing interest in electrophosphorescent materials, particularly metal complexes with heavy metal centers, most efforts have been focused on the use of iridium(III), platinum(II) and ruthenium(II). Other metal centers have had very little attention. In contrast to isoelectronic platinum(II) compounds that are known to show rich luminescence properties, very few examples of luminescent gold(III) complexes have been reported, which probably stems from the presence of low-energy d-d ligand field (LF) states and the electrophilicity observed for gold(III) metal center. One way to enhance luminescence of gold(III) complexes is by introduction of strong σ-donating ligands, as first demonstrated by Yam et al. for stable gold(III) aryl compounds found to display interesting photoluminescence properties even at room temperature [Yam, V. W. W.; Choi, S. W. K.; Lai, T. F.; Lee, W. K. *J. Chem. Soc., Dalton Trans.* 1001 (1993)]. Another interesting donor ligand is the alkynyl group. Although the luminescence properties of gold(I) alkynyls have been extensively studied, the chemistry of gold(III) alkynyls has been essentially ignored, the exception being a brief report on the synthesis of an alkynylgold(III) compound of 6-benzyl-2,2'-bipyridine [Cinellu, M. A.; Minghetti, G.; Pinna, M. V.; Stoccoro, S.; Zucca, A.; Manassero, M. *J. Chem. Soc. Dalton Trans.* 2823 (1999)], but its luminescence behaviour has remained unexplored. Yam et al. discloses the synthesis of a series of bis-cyclometalated alkynylgold(III) compounds using various strong σ-donating alkynyl ligands with all compounds exhibiting rich luminescence behaviors at both room and low temperatures in various media [Yam, V. W.-W.; Wong, K. M.-C.; Hung, L.-L.; Zhu, N. *Angew. Chem. Int. Ed.* 44, 3107 (2005); Wong, K. M.-C.; Zhu, X.; Hung, L.-L.; Zhu, N.; Yam, V. W.-W.; Kwok, H. S. *Chem. Commun.* 2906 (2005); Wong, K. M.-C.; Hung, L.-L.; Lam, W. H.; Zhu, N.; Yam, V. W.-W. *J. Am. Chem. Soc.* 129, 4350 (2007)]. In addition, the utilization of these luminescent gold(III) compounds as phosphorescent dopant materials in OLEDs yields strong electroluminescence with high external quantum efficiencies of about 5.5%. These luminescence gold(III) compounds contain one tridentate ligand and at least one strong σ-donating group coordinated to a gold(III) metal center.

BRIEF SUMMARY OF THE INVENTION

Embodiments of the invention are directed to novel luminescent gold(III) compounds. Other embodiments of the invention are directed to a method to prepare the novel luminescent gold(III) compounds. Other embodiments of the invention are directed to light-emitting devices from the novel luminescent gold(III) compounds.

The novel luminescent gold(III) compounds are coordination compounds that contain a bidentate ligand and at least one strong σ-donating group coordinated to a gold(III) metal center.

The novel luminescent gold(III) compounds have the chemical structure:

wherein:
X is a nitrogen atom;
Y is selected from a carbon or a nitrogen atom;
A-B is a substituted or unsubstituted cyclometalating ligand (for Y=C) or diimine ligand (for Y=N);
A and B are cyclic structure derivatives;
$R_1$ and $R_2$ are optionally substituted carbon donor ligands, where $R_1$ and $R_2$ are not —$CH_3$, —$CH_2SiMe_3$, mesityl, pentafluorophenyl, —$CH_2C(O)R'$, —$CH(R)SO_2CH(R)$—, —$C_6H_4N$=$NC_6H_5$, and wherein $R_1$ and $R_2$ can either be connected to or separated from each other; n is zero or an integer.

The luminescent gold(III) compounds according to embodiments of the invention show strong photoluminescence via triplet excited state upon photo-excitation, or electroluminescence via triplet exciton upon applying a DC voltage. Many compounds according to embodiments of the invention are thermally stable and volatile enough to be able to form a thin layer by sublimation or vacuum deposition. Alternatively, the compounds can be doped into a host matrix for thin film deposition by spin-coating or inkjet printing or other known fabrication methods. The compounds can be used for the fabrication of OLEDs as phosphorescent emitters or dopants to generate electroluminescence.

In an OLED according to an embodiment of the present invention, the luminescent gold(III) compound is included in a light-emitting layer. The structure of the OLED comprising the luminescent gold(III) compounds of the present invention can comprise a layer structure having a cathode layer, an electron transporting layer, the luminescent gold(III) compound as the light-emitting layer, a carrier confinement layer, a hole transporting layer and an anode.

DETAILED DESCRIPTION OF THE INVENTION

Embodiments of the invention are directed to a novel class of luminescent gold(III) compounds with a bidentate ligand and at least one strong σ-donating group. Other embodiments of the invention are directed to the synthesis of these luminescent gold(III) compounds. The novel compounds comprise:

at least one gold metal center having a +3 oxidation state and four coordination sites;

one bidentate ligand with one to two aromatic or heterocyclic ring(s) coordinating to two coordination sites of the gold metal center; and two monodentate ligands or a second bidentate ligand coordinating to two coordination sites of the gold metal center, wherein at least one ligand is a strong σ-donating ligand and wherein the compound is neutral or positively charged.

The compounds have the chemical structure shown in generic formula (I):

(I)

wherein:
(a) X is a nitrogen atom;
(b) Y is selected from a carbon or a nitrogen atom;
(c) A-B is a substituted or unsubstituted cyclometalating ligand (for Y=C) or diimine ligand (for Y=N);
(d) A and B are cyclic structure derivatives;
(e) $R_1$ and $R_2$ are optionally substituted carbon donor ligands attached to the gold atom, with the proviso that $R_1$ and $R_2$ are not —$CH_3$, —$CH_2SiMe_3$, mesityl, pentafluorophenyl, —$CH_2C(O)R'$, —CH(R)$SO_2$CH(R)—, —$C_6H_4N$=$NC_6H_5$, and wherein $R_1$ and $R_2$ can either be connected to or separated from each other;
(f) n is zero or an integer.

Rings A and B are cyclic structure derivatives where the cyclic structures are independently selected from a 5- or 6-membered arene, heteroarene or heterocycle known in the art, where ring A is a nitrogen containing heteroarene or heterocycle. The arene or heteroarene can be benzene, pyridine, thiophene, furan, pyrazole, imidazole, oxazole, isoxazole, thiazole, isothiazole, isoquinoline, pyrrole, pyrazine, pyridazine, pyrimidine, benzimidazole, benzofuran, benzothiazole, indole, naphthalene, anthracene, pyrene, triazole, tetrazole, pyran, thiapyran, oxadiazole, triazine, tetrazine, carbazole, dibenzothiophene, dibenzofuran, fluorene and derivatives thereof.

Rings A and B can be unsubstituted or can be substituted with one or more alkyl, alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3R$, halo, aryl, substituted aryl, heteroaryl, substituted heteroaryl or a heterocyclic group, and additionally, or alternatively, any two adjacent substituted positions of rings A and B together form, independently, a fused 5- to 6-member cyclic group, wherein said cyclic group is cycloalkyl, cycloheteroalkyl, aryl, or heteroaryl, and wherein the fused 5- to 6-member cyclic group may be substituted with one or more of alkyl, alkenyl, alkynyl, alkylaryl, cycloalkyl, CN, $CF_3$, C(O)OR, C(O)R, $NR_2$, $NO_2$, OR, or halo; and each R is independently alkyl, alkenyl, alkynyl, alkylaryl, aryl and cycloalkyl.

The cyclometalating ligand, A-B (for Y=C), and the diimine ligand, A-B (for Y=N), are selected from those known in the art. For example, cyclometalating ligands can be, but are not limited to, 2-phenylpyridines, phenylisoquinolines, phenylpyrazoles, 7,8-benzoquinolines and derivatives thereof, and diimine ligands can be, but are not limited to, 2,2'-bipyridines, 1,10-phenanthrolines and derivatives thereof. The cyclometalated and diimine ligands can be unsubstituted or can be substituted with one or more alkyl, alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3R$, halo, aryl, substituted aryl, heteroaryl, substituted heteroaryl or a heterocyclic group, and additionally, or alternatively, one or more pairs of adjacent substituted positions not including an atom ligating the gold(III) can in combination form, independently, a fused 5- to 6-member cyclic group, wherein the cyclic group is cycloalkyl, cycloheteroalkyl, aryl, or heteroaryl, and, optionally, where the fused 5- to 6-member cyclic group may be substituted with one or more of alkyl, alkenyl, alkynyl, alkylaryl, cycloalkyl, OR, C(O)R, C(O)OR, C(O)$NR_2$, CN, $CF_3$, $NR_2$, $NO_2$, SR, $SO_2$, SOR, $SO_3R$, and halo where R is independently alkyl, alkenyl, alkynyl, alkylaryl, aryl and cycloalkyl.

The term "halo" or "halogen" indicates a fluorine, chlorine, bromine and iodine. The term "alkyl" indicates either a straight or branched chain alkyl groups. The alkyl groups contain from one to eighteen or more carbon atoms, including methyl, ethyl, propyl, isopropyl, butyl, isobutyl, tert-butyl, and the like. In addition, the alkyl group may be unsubstituted or substituted with one or more substituents including, but not limited to, OR, $NR_2$, SR, C(O)R, C(O)OR, C(O)$NR_2$, CN, $CF_3$, $NO_2$, $SO_2$, SOR, $SO_3R$, halo and cyclic-amino.

The term "alkenyl" as used herein includes both straight and branched chain alkene radicals of two to eighteen or more carbon atoms. The alkenyl group may be unsubstituted or substituted with one or more substituents including, but not limited to, OR, $NR_2$, SR, C(O)R, C(O)OR, C(O)$NR_2$, CN, $CF_3$, $NO_2$, $SO_2$, SOR, $SO_3R$, halo and cyclic-amino.

The term "alkynyl" as used herein includes both straight and branched chain alkyne radicals of two to eighteen or more carbon atoms. The alkynyl group can be unsubstituted or substituted with one or more substituents including, but not limited to, OR, $NR_2$, SR, C(O)R, C(O)OR, C(O)$NR_2$, CN, $CF_3$, $NO_2$, $SO_2$, SOR, $SO_3R$, halo and cyclic-amino.

The term "arylalkynyl" as used herein includes an alkynyl group which has an aromatic group as a substituent. The arylalkynyl group may be unsubstituted or substituted with one or more substituents including, but not limited to, OR, $NR_2$, SR, C(O)R, C(O)OR, C(O)$NR_2$, CN, $CF_3$, $NO_2$, $SO_2$, SOR, $SO_3R$, halo and cyclic-amino.

The term "alkylaryl" as used herein includes an alkyl group which has an aromatic group as a substituent. The alkylaryl group may be unsubstituted or substituted with one or more substituents including, but not limited to, OR, $NR_2$, SR, C(O)R, C(O)OR, C(O)$NR_2$, CN, $CF_3$, $NO_2$, $SO_2$, SOR, $SO_3R$, halo and cyclic-amino.

The term "cycloalkyl" as used herein includes cyclic alkyl groups. Cycloalkyl groups can contain 3 to 7 or more carbon atoms and include cyclopropyl, cyclopentyl, cyclohexyl, and the like. Cycloalkyl groups may be unsubstituted or substituted with one or more substituents including, but not limited to, OR, $NR_2$, SR, C(O)R, C(O)OR, C(O)$NR_2$, CN, $CF_3$, $NO_2$, $SO_2$, SOR, $SO_3R$, halo and cyclic-amino.

The term "alkoxy" as used herein includes linear or branched alkoxy groups of one to eighteen or more carbon atoms, and can be unsubstituted or substituted with one or more substituents including, but not limited to, OR, $NR_2$, SR, C(O)R, C(O)OR, C(O)$NR_2$, CN, $CF_3$, $NO_2$, $SO_2$, SOR, $SO_3R$, halo and cyclic-amino.

Aryl alone or in combination includes carbocyclic aromatic systems containing one, two or three rings, wherein each ring may be attached together in a pendent manner or may be fused and can be 5- or 6-membered rings. The aryl rings can be unsubstituted or substituted with one or more substituents including, but not limited to, OR, $NR_2$, SR, C(O)R, C(O)OR, C(O)$NR_2$, CN, $CF_3$, $NO_2$, $SO_2$, SOR, $SO_3R$, halo and cyclic-amino.

Heteroaryl alone or in combination includes heterocyclic aromatic systems which contain one, two, three or more rings, wherein each ring may be combined in a pendent or fused manner, wherein each ring of the system is a 5- or 6-membered rings.

Heterocyclic and heterocycle refer to a 3 to 7-membered ring containing at least one heteroatom. The heterocyclic rings can be aromatic, including, but not limited to, pyridine, thiophene, furan, pyrazole, imidazole, oxazole, isoxazole, thiazole, isothiazole, isoquinoline, pyrrole, pyrazine, pyridazine, pyrimidine, benzimidazole, benzofuran, benzothiazole, indole, naphthalene, triazole, tetrazole, pyran, thiapyran, oxadiazole, triazine, tetrazine, carbazole, dibenzothiophene, dibenzofuran, indole, and fluorine. The heterocyclic rings can be non-aromatic, including, but not limited to, piperazine, piperidine, and pyrrolidine. Heterocyclic rings can be unsubstituted or substituted, which can include, but are not limited to, alkyl, alkoxy, aryl. The hetero atom can be S, O, N or P.

Cyclometalating ligand is a term well known in the art and includes, but is not limited to, 2-phenylpyridine (ppy), 2-(p-tolyl)pyridine (ptpy), 4-(2-pyridyl)benzaldehyde (pba), 2-(2,4-difluorophenyl)pyridine (fppy), 4-pyridin-2-ylbenzoic acid, 3-pyridin-2-ylbenzoic acid, 2-methyl-6-phenylpyridine, 3-methyl-2-phenylpyridine, 4-methyl-2-phenylpyridine, 5-methyl-2-phenylpyridine, 2-phenylpyridine-3-carboxylic acid, 2-phenylpyridine-4-carboxylic acid, 6-phenylpyridine-3-carboxylic acid, 2,3-diphenylpyridine, 2,4-diphenylpyridine, 2,5-diphenylpyridine, phenylpyrazole (ppz), 3-methyl-1-phenyl-1H-pyrazole (mppz), 7,8-benzoquinoline (bzq), 2-phenylquinoline (pq), 1-phenylisoquinoline (piq), 2-phenylquinoline, 3-phenylisoquinoline, 3,4-diphenylisoquinoline and 2-(benzimidazol-2-yl)quinoline (biq).

Diimine ligand is a term well known in the art and includes, but not limited to, 2,2'-bipyridine (bpy), 4-chloro-2,2'-bipyridine (4-Cl-bpy), 4-methyl-2,2'-bipyridine (4-Me-bpy), 4-carboxy-2,2'-bipyridine, 4,4'-dimethyl-2,2'-bipyridine (4,4'-$Me_2$-bpy), 4,4'-diethyl-2,2'-bipyridine (4,4'-$Et_2$-bpy), 4,4'-di-tert-butyl-2,2'-bipyridine (4,4'-$^tBu_2$-bpy), 4,4'-diphenyl-2,2'-bipyridine (4,4'-$Ph_2$-bpy), 4,4'-dihexyl-2,2'-bipyridine, 4,4'-dioctyl-2,2'-bipyridine, 4,4'-dicarboxy-2,2'-bipyridine, 4,4'-bis(methoyxcarbonyl)-2,2'-bipyridine, 4,4'-bis(ethoxycarbonyl)-2,2'-bipyridine, 5,5'-bis(ethoxycarbonyl)-2,2'-bipyridine, 5,5'-dicarboxy-2,2'-bipyridine, 5-carboxy-2,2'-bipyridine, 5-methyl-2,2'-bipyridine, 6-bromo-2,2'-bipyridine, 5-chloro-2,2'-bipyridine, 1,10-phenanthroline (phen), 4-chloro-1,10-phenanthroline (4-Cl-phen), 4-methyl-1,10-phenanthroline (4-Me-phen), 5-chloro-1,10-phenanthroline (5-Cl-phen), 5-bromo-1,10-phenanthroline (5-Br-phen), 5-phenyl-1,10-phenanthroline (5-Ph-phen), 5-nitro-1,10-phenanthroline (5-$NO_2$-phen), 5-amino-1,10-phenanthroline (5-$NH_2$-phen), 5-methyl-1,10-phenanthroline (5-$Me_2$-phen), 4,7-dimethyl-1,10-phenanthroline (4,7-$Me_2$-phen), 4,7-diphenyl-1,10-phenanthroline (4,7-$Ph_2$-phen), 4,7-bis(4-bromophenyl)-1,10-phenanthro line, 4,7-bis(biphenyl)-1,10-phenanthroline, 5,6-dimethyl-1,10-phenanthro line (5,6-$Ph_2$-phen), 3,4,7,8-tetramethyl-1,10-phenanthroline (3,4,7,8-$Me_4$-phen), 3-bromo-1,10-phenanthroline (3-Br-phen), 3,8-dibromo-1,10-phenanthro line (3,8-$Br_2$-phen), 5,6-dibromo-1,10-phenanthroline (5,6-$Br_2$-phen), 2,9-dichloro-1,10-phenanthroline (2,9-$Cl_2$-phen), 2,9-dimethyl-1,10-phenanthroline (2,9-$Me_2$-phen), 2,9-dimethyl-4,7-diphenyl-1,10-phenanthroline (2,9-$Me_2$-4,7-$Ph_2$-phen), 5-carboxy-1,10-phenanthro line, 5-isothiocyanato-1,10-phenanthroline, dipyrido[3,2-a:2',3'-c]phenazine (dppz) and benzo[i]dipyrido[3,2-a:2',3'-c]phenazine (dppn), 2-(2-thienyl)pyridine and 3-(2-thienyl)pyridine.

Benzene includes substituted or unsubstituted benzene.
Pyridine includes substituted or unsubstituted pyridine.
Thiophene includes substituted or unsubstituted thiophene.
Furan includes substituted or unsubstituted furan.
Pyrazole includes substituted or unsubstituted pyrazole.
Imidazole includes substituted or unsubstituted imidazole.
Oxazole includes substituted or unsubstituted oxazole.
Isoxazole includes substituted or unsubstituted isoxazole.
Thiazole includes substituted or unsubstituted thiazole.
Isothiazole includes substituted or unsubstituted isothiazole.
Isoquinoline includes substituted or unsubstituted isoquinoline.
Pyrrole includes substituted or unsubstituted pyrrole.
Pyrazine includes substituted or unsubstituted pyrazine.
Pyridazine includes substituted or unsubstituted pyridazine.
Pyrimidine includes substituted or unsubstituted pyrimidine.
Benzimidazole includes substituted or unsubstituted benzimidazole.
Benzofuran includes substituted or unsubstituted benzofuran.
Benzothiazole includes substituted or unsubstituted benzothiazole.
Indole includes substituted or unsubstituted indole.
Naphthalene includes substituted or unsubstituted naphthalene.
Anthracene includes substituted or unsubstituted anthracene.
Pyrene includes substituted or unsubstituted pyrene.
Triazole includes substituted or unsubstituted triazole.
Tetrazole includes substituted or unsubstituted tetrazole.
Pyran includes substituted or unsubstituted pyran.
Thiapyran includes substituted or unsubstituted thiapyran.
Oxadiazole includes substituted or unsubstituted oxadiazole.
Triazine includes substituted or unsubstituted triazine.
Tetrazine includes substituted or unsubstituted tetrazine.
Carbazole includes substituted or unsubstituted carbazole.
Dibenzothiophene includes substituted or unsubstituted dibenzothiophene.
Dibenzofuran includes substituted or unsubstituted dibenzofuran.

Fluorene includes substituted or unsubstituted fluorene.
Piperazine includes substituted or unsubstituted piperazine.
Piperidine includes substituted or unsubstituted piperidine.
Pyrrolidine includes substituted or unsubstituted pyrrolidine.

The present invention is illustrated by the following non-limiting examples. It is to be understood that changes and variations can be made therein without deviating from the scope and the spirit of the invention as hereinafter claimed. It is also understood that various theories as to why the invention works are not intended to be limiting. The compounds described herein are represented throughout by their monomeric structure. As is well known to those in the art, the compounds may also be present as dimers, trimers, larger oligomers or dendrimers.

In other embodiments of the invention the luminescent gold(III) compounds of structure (I) are prepared in high purity. The synthetic method involves providing a gold(III) dichloride or its equivalent that is complexed with a cyclometalating ligand or diimine ligand, for example a 2-phenylpyridine or 2,2'-bipyridine, respectively. The complexed gold (III) dichlorides can be prepared by any method known to those skilled in the art, for example the methods disclosed in Constable et al., *J. Organomet. Chem.* 363, 419 (1989) and Cinellu et al., *J. Chem. Soc., Dalton Trans.* 1261 (2000), which are incorporated herein by reference. The gold(III) complex subsequently undergoes reaction with a strong σ-donating ligand precursor, for example an alkali alkynyl metal, arylalkynyl metal, substituted alkynyl metal or substituted, arylalkynyl metal that involves displacement of at least one of the chlorides of the complexed gold(III) dichloride to form the novel luminescent gold(III) compounds of structure (I), as can be appreciated upon inspection of Schemes 1-4, below where the metal is the alkali metal, lithium. Although the method can vary depending upon the σ-donating ligand desired, in general the reactions are carried out in solution. The reactions are generally carried out below normal room temperatures and can be carried out at very low temperatures, for example −78° C., the temperature of a dry ice-acetone bath. Specific conditions of solvent and temperature vary depending upon the structure of the desired gold(III) compound, as can be appreciated by those skilled in the art. Purification can be carried out by any method or combination of methods, including chromatography, extraction, crystallization, sublimation or any combination thereof.

The luminescent gold(III) compounds can be used to form an organic light emitting device (OLED) according to embodiments of the invention. Light emitting devices can be used in displays or solid state lighting applications, and can be used those that function through photoluminescence or electroluminescence processes. The novel gold(III) compounds can be the primary luminescent material or a secondary luminescent material in the device. The novel gold(III) compounds can be employed as electrophosphorescent dopants in a multilayer OLED with a quantum efficiency of up to 5.5% or more. Advantageously, the novel gold(III) compounds can be deposited in the OLEDs by vacuum deposition or liquid deposition techniques.

EXAMPLE 1

Synthesis and Characterization

Compounds 1-17 were prepared according to the following methodology as illustrated in Scheme 1 below. Compound 18 and 19 were prepared using the methodology shown in Schemes 2 and 3, respectively, whereas compounds 20-22 were prepared according to Scheme 4. The precursor compound, [Au(C^N)Cl$_2$] and [Au(N^N)Cl$_2$]PF$_6$, were prepared as disclosed in Constable et al., *J. Organomet. Chem.* 363, 419 (1989) and Cinellu et al., *J. Chem. Soc., Dalton Trans.* 1261 (2000), which are incorporated herein by reference. Compounds 1-22, with the exception of compound 18, were synthesized by the reaction of the respective precursor compounds with various alkynylating reagents. Compound 18, as shown in Scheme 2, is prepared from compound 16 where the —Si(CH$_3$)$_3$ group acts as a protecting group that can be removed or "deprotected" by reaction with a deprotecting agent, such as a fluoride ion, which is a strong nucleophile towards Si. As indicated in Scheme 2, the fluoride ion is provided by tetrabutylammonium fluoride, or alternatively any other fluoride ion source, which is available commercially in solution. For example, to prepare compound 1, n-butyllithium was added dropwise to a solution of 4-methoxyphenylacetylene in tetrahydrofuran under a nitrogen atmosphere at −78° C. The resulting mixture was stirred for 5 minutes and transferred to a suspension of [Au(ppy)Cl$_2$] (ppy=2-phenylpyridine). The reaction mixture was stirred for 3 hours at room temperature. The crude product was purified by column chromatography on silica gel using dichloromethane as eluent. Pale yellow crystals were obtained from slow diffusion of diethyl ether into the dichloromethane solution of the compounds.

Scheme 1

| | R | R' | X | n | R$_1$ |
|---|---|---|---|---|---|
| (1) | H | H | C | 0 | C≡C—C$_6$H$_4$—OCH$_3$-p |
| (2) | CH$_3$ | H | C | 0 | C≡C—C$_6$H$_4$—OCH$_3$-p |
| (3) | H | H | N | 1 | C≡C—C$_6$H$_4$—OCH$_3$-p |
| (4) | CH$_3$ | H | C | 0 | C≡C—C$_6$H$_4$—C$_4$H$_9$-p |
| (5) | H | H | C | 0 | C≡C—C$_6$H$_4$—C$_2$H$_5$-p |
| (6) | H | H | C | 0 | C≡C—C$_6$H$_4$—CF$_3$-p |
| (7) | OCH$_3$ | 5-CH$_3$ | C | 0 | C≡C—C$_6$H$_4$—OCH$_3$-p |
| (8) | $^t$Bu | H | C | 0 | C≡C—C$_6$H$_4$—OCH$_3$-p |
| (9) | H | H | C | 0 | C≡C—C$_6$H$_4$—NH$_2$-p |
| (10) | CH$_3$ | H | C | 0 | C≡C—C$_6$H$_4$—NH$_2$-p |
| (11) | H | H | C | 0 | C≡C—C$_6$H$_4$—N(CH$_3$)$_2$-p |
| (12) | CH$_3$ | H | C | 0 | C≡C—C$_6$H$_4$—N(CH$_3$)$_2$-p |
| (13) | OCH$_3$ | H | C | 0 | C≡C—C$_6$H$_4$—OCH$_3$-p |
| (14) | OCH$_3$ | 4-CH$_3$ | C | 0 | C≡C—C$_6$H$_4$—OCH$_3$-p |
| (15) | OCH | 5-CF$_3$ | C | 0 | C≡C—C$_6$H$_4$—OCH$_3$-p |
| (16) | H | H | C | 0 | C≡C—Si(CH$_3$)$_3$ |
| (17) | CH$_3$ | H | C | 0 | C≡C—Si(CH$_3$)$_3$ |

Scheme 2

Scheme 3

Scheme 4

The characteristic spectroscopic properties of compounds 1-22 are as follows:

Compound 1 [Au(ppy)(C≡C—$C_6H_4$—$OCH_3$-p)$_2$] (ppy=2-phenylpyridine) Yield: 33%. $^1$H NMR (400 MHz, CDCl$_3$, 298 K, relative to Me$_4$Si): δ 3.82 (s, 6H, —OCH$_3$), 6.85 (m, 4H, phenyl), 7.39 (m, 1H, ppy), 7.41 (m, 2H), 7.50-7.56 (m, 4H, phenyl), 7.67 (d, 5.7 Hz, 1H, ppy), 7.90 (d, 6.0 Hz, 1H, ppy), 8.06 (t, 6.5 Hz, 1H, ppy), 8.30 (d, 7.5 Hz, 1H, ppy), 9.71 (d, 4.8 Hz, 1H, ppy); positive FAB-MS: m/z 614 [M]$^+$; IR (KBr): 2120 cm$^{-1}$, 2167 cm$^{-1}$; elemental analyses calcd for $C_{29}H_{22}NO_2Au$ (found): C, 56.78 (56.94); H, 3.61 (3.87); N, 2.28 (2.32).

Compound 2 [Au(ptpy)(C≡C—$C_6H_4$—$OCH_3$-p)$_2$] (ptpy=2-(p-tolyl)pyridine) Yield: 60%. $^1$H NMR (300 MHz, CDCl$_3$, 298 K, relative to Me$_4$Si): δ 2.41 (s, 3H, —CH$_3$), 3.82 (s, 6H, —OCH$_3$), 6.85 (m, 4H, phenyl), 7.14 (d, 7.9 Hz, 1H, ptpy), 7.36 (t, 7.2 Hz, 1H, ptpy), 7.57-7.37 (m, 5H, ptpy and phenyl), 7.83 (d, 8.0 Hz, 1H, ptpy), 7.99 (t, 7.5 Hz, 1H, ptpy), 8.11 (s, 1H, ptpy), 9.66 (d, 5.7 Hz, 1H, ptpy); positive FAB-MS: m/z 532 [M]$^+$; IR (KBr): 2130 cm$^{-1}$, 2163 cm$^{-1}$; elemental analyses calcd for $C_{30}H_{24}NO_2Au·½CH_3OH$ (found): C, 56.93 (56.90); H, 4.07 (3.87); N, 2.18 (2.31).

Compound 3 [Au(bpy)(C≡C—$C_6H_4$—$OCH_3$-p)$_2$]PF$_6$ (bpy=2,2'-bipyridine) Yield: 15%. $^1$H NMR (400 MHz, acetone-d$_6$, 298 K, relative to Me$_4$Si): δ 3.73 (s, 6H, —CH$_3$), 6.72 (d, 6.8 Hz, 4H, phenyl), 8.68 (d, 4.0 Hz, 2H, bpy), 7.14 (d, 6.8 Hz, 4H, phenyl), 7.43 (t, 4.8 Hz, 2H, bpy), 7.94 (t, 7.8 Hz, 2H, bpy), 8.47 (d, 8.0 Hz, 2H, bpy).

Compound 4 [Au(ptpy)(C≡C—$C_6H_4$—$C_4H_9$-p)$_2$] (ptpy=2-(p-tolyl)pyridine) Yield: 39%. $^1$H NMR (400 MHz, CD$_2$Cl$_2$, 298 K, relative to Me$_4$Si): δ 0.94 (m, 6H, —CH$_3$), 1.38 (m, 4H, —CH$_2$—), 1.59 (m, 4H, —CH$_2$—), 2.38 (s, 3H, —CH$_3$), 2.61 (m, 4H, —CH$_2$—), 7.15 (m, 5H, ptpy and phenyl), 7.36 (m, 1H, ptpy), 7.43 (dd, 8.1 Hz and 4.7 Hz, 4H, phenyl), 7.58 (d, 8.1 Hz, 1H, ptpy), 7.85 (d, 8.1 Hz, 1H, ptpy), 7.99 (m, 2H, ptpy), 9.57 (dd, 1.1 and 4.7 Hz, 1H, ptpy); positive FAB-MS: m/z 522 [M-C≡CC$_6$H$_4$—C$_4$H$_9$]$^+$; IR (KBr): 2113 cm$^{-1}$, 2167 cm$^{-1}$; elemental analyses calcd for $C_{36}H_{36}NAu$ (found): C, 63.62 (63.80); H, 5.34 (5.56); N, 2.06 (2.29).

Compound 5 [Au(ppy)(C≡C—C₆H₄—C₂H₅-p)₂] (ppy=2-phenylpyridine) Yield: 28%. ¹H NMR (400 MHz, CDCl₃, 298 K, relative to Me₄Si): δ 1.24 (s, 6H, —CH₃), 2.65 (m, 4H, —CH₂—), 7.14 (m, 4H, phenyl), 7.38 (m, 3H, ppy), 7.51 (m, 4H, phenyl), 7.66 (d, 7.0 Hz, 1H, ppy), 7.89 (m, 1H, ppy), 8.04 (s, 1H, ppy), 8.27 (d, 7.0 Hz, 1H, ppy), 9.67 (s, 1H, ppy); positive FAB-MS: m/z 609 [M]⁺; IR (KBr): 2136 cm⁻¹, 2163 cm⁻¹; elemental analyses calcd for C₃₁H₂₆NAu.½C₅H₁₂ (found): C, 62.32 (62.31); H, 5.00 (4.60); N, 2.17 (2.52).

Compound 6 [Au(ppy)(C≡C—C₆H₄—CF₃-p)₂] (ppy=2-phenylpyridine) Yield: 28%. ¹H NMR (400 MHz, CD₂Cl₂, 298 K, relative to Me₄Si): δ 7.40 (m, 2H, ppy), 7.48 (m, 1H, ppy), 7.57 (m, 4H, phenyl), 7.65 (m, 4H, phenyl), 7.66 (m, 1H, ppy), 7.94 (d, 8.1 Hz, 1H, ppy), 8.09 (dt, 1.3 and 7.3 Hz, 1H, ppy), 8.17 (dd, 1.3 and 7.3 Hz, ppy); positive FAB-MS: m/z 689 [M]⁺; IR (KBr): 2136 cm⁻¹, 2166 cm⁻¹; elemental analyses calcd for C₂₉H₁₆NF₆Au (found): C, 50.52 (50.35); H, 2.34 (2.36), N, 2.03 (2.08).

Compound 7 [Au(mpmepy)(C≡C—C₆H₄—OCH₃-p)₂] (mpmepy=5-methyl-2-(p-methoxyphenyl)pyridine) Yield: 30%. ¹H NMR (300 MHz, CD₂Cl₂, 298 K, relative to Me₄Si): δ 2.40 (s, 3H, —CH₃), 3.80 (s, 6H, —OCH₃), 3.85 (s, 3H, —OCH₃), 6.85 (m, 5H, mpmepy and phenyl), 7.49 (m, 4H, phenyl), 7.64 (q, 8.3 Hz, 2H, mpmepy), 7.81 (m, mpmepy), 9.40 (s, 1H, mpmepy); positive FAB-MS: m/z 657 [M]⁺; IR (KBr): 2132 cm⁻¹, 2161 cm⁻¹; elemental analyses calcd for C₃₁H₂₆NO₃Au.½H₂O (found): C, 55.86 (55.85); H, 4.08 (3.94); N, 2.10 (2.21).

Compound 8 [Au(tbppy)(C≡C—C₆H₄—OCH₃-p)₂] (tbppy=2-(p-(tert-butyl)phenyl)pyridine) Yield: 21%. ¹H NMR (300 MHz, CD₂Cl₂, 298 K, relative to Me₄Si): δ 1.36 (s, 9H, ᵗBu), 3.80 (s, 6H, —OCH₃), 6.86 (m, 4H, phenyl), 7.40 (m, 2H, tbppy), 7.48 (m, 4H, phenyl), 7.65 (d, 8.2 Hz, 1H, tbppy), 7.89 (d, 7.9 Hz, 1H, tbppy), 8.02 (t, 7.9 Hz, 1H, tbppy), 8.38 (d, 1.9 Hz, 1H, tbppy), 9.64 (d, 5.0 Hz, tbppy); positive FAB-MS: m/z 669 [M]⁺; IR (KBr): 2098 cm⁻¹, 2189 cm⁻¹; elemental analyses calcd for C₃₃H₃₀NO₂Au.½H₂O (found): C, 58.41 (58.36); H, 4.60 (4.60); N, 2.06 (1.99).

Compound 9 [Au(ppy)(C≡C—C₆H₄—NH₂-p)₂] (ppy=2-phenylpyridine) Yield: 55%. ¹H NMR (400 MHz, DMSO-d₆, 298 K, relative to Me₄Si): δ 5.24 (s, 2H, —NH₂), 5.30 (s, 2H, —NH₂), 6.56 (m, 4H, phenyl), 7.17 (dd, 2.5 and 5.6 Hz, 4H, phenyl), 7.41 (m, 2H, ppy), 7.75 (m, 1H, ppy), 8.01 (d, 7.6 Hz, 1H, ppy), 8.16 (d, 7.6 Hz, 1H, ppy), 8.34 (m, 2H, ppy), 9.57 (d, 5.6 Hz, ppy); positive FAB-MS: m/z 584 [M]⁺; elemental analyses calcd for C₂₇H₂₀N₃Au.½H₂O (found): C, 54.74 (54.81); H, 3.57 (3.40); N, 7.09 (7.09).

Compound 10 [Au(ptpy)(C≡C—C₆H₄—NH₂-p)₂] (ptpy=2-(p-tolyl)pyridine) Yield: 19%. ¹H NMR (400 MHz, DMSO-d₆, 298 K, relative to Me₄Si): δ 2.38 (s, 3H, —CH₃), 5.28 (s, 2H, —NH₂), 5.35 (s, 2H, —NH₂), 6.54 (m, 4H, phenyl), 7.17 (m, 4H, phenyl), 7.72 (m, 1H, ptpy), 7.92 (d, 8.0 Hz, 1H, ptpy), 7.98 (s, 1H, ptpy), 8.31 (m, 2H, ptpy), 9.53 (d, 5.6 Hz, 1H); positive FAB-MS: m/z 597 [M]⁺; elemental analyses calcd for C₂₈H₂₂N₃Au.½H₂O (found): C, 56.29 (55.99); H, 3.71 (3.74); N, 7.03 (7.00).

Compound 11 [Au(ppy)(C≡C—C₆H₄—N(CH₃)₂-p)₂] (ppy=2-phenylpyridine) Yield: 22%. ¹H NMR (400 MHz, DMSO-d₆, 298 K, relative to Me₄Si): δ 2.91 (s, 6H, —N(CH₃)₂), 3.21 (s, 6H, —N(CH₃)₂), 6.58 (d, 8.9 Hz, 2H, phenyl), 7.06 (d, 8.7 Hz, 2H, phenyl), 7.23 (d, 8.9 Hz, 2H, phenyl), 7.51 (d, 8.7 Hz, 2H, phenyl), 7.66 (t, 7.9 Hz, 2H, ppy), 7.79 (d, 7.9 Hz, 1H, ppy), 7.85 (t, 8.2 Hz, 1H, ppy), 8.20 (t, 8.5 Hz, 1H, ppy), 8.73 (d, 7.9 Hz, 1H, ppy), 8.86 (d, 7.2 Hz, 1H, ppy), 9.07 (d, 8.2 Hz, 1H, ppy); positive FAB-MS: m/z 639 [M]⁺; elemental analyses calcd for C₃₁H₂₈AuN₃.2H₂O (found): C, 55.11 (55.04); H, 4.77 (4.45); N, 6.22 (6.03).

Compound 12 [Au(ptpy)(C≡C—C₆H₄—N(CH₃)₂-p)₂] (ptpy=2-(p-tolyl)pyridine) Yield: 31%. ¹H NMR (300 MHz, CD₂Cl₂, 298 K, relative to Me₄Si): δ 2.63 (s, 3H, —CH₃), 2.89 (s, 6H, —N(CH₃)₂), 3.08 (s, 6H, —N(CH₃)₂), 6.56 (d, 8.7 Hz, 2H, phenyl), 6.92 (d, 8.7 Hz, 2H, phenyl), 7.19 (d, 8.6 Hz, 2H, phenyl), 7.43 (d, 8.6 Hz, 2H, phenyl), 7.48 (d, 6.8 Hz, 1H, ptpy), 7.65 (d, 8.9 Hz, 1H, ptpy), 8.03 (t, 7.6 Hz, 1H, ptpy), 8.56 (d, 8.4 Hz, 1H, ptpy), 8.75 (d, 7.3 Hz, 1H, ptpy), 8.89 (d, 8.4 Hz, 1H, ptpy), 8.94 (s, 1H, ptpy); positive-ion FAB-MS: m/z 654 [M]⁺; elemental analyses calcd for C₃₂H₃₀AuN₃.½CH₂Cl₂ (found): C, 56.08 (56.02); H, 4.49 (4.40); N, 6.04 (6.17).

Compound 13 [Au(mppy)(C≡C—C₆H₄—OCH₃-p)₂] (mppy=2-(p-methoxyphenyl)pyridine) Yield: 14%. ¹H NMR (300 MHz, CD₂Cl₂, 298 K, relative to Me₄Si): δ 3.80 (s, 6H, —OCH₃), 3.87 (s, 3H, —CH₃), 6.85 (m, 5H, phenyl and mppy), 7.33 (t, 7.8 Hz, 1H, mppy), 7.47 (m, 4H, phenyl), 7.68 (d, 7.8 Hz, 1H, mppy), 7.78 (d, 7.8 Hz, 1H, mppy), 7.85 (d, 2.6 Hz, 1H, mppy), 8.00 (t, 7.8 Hz, 1H, mppy), 9.56 (m, 1H, mppy); positive FAB-MS: m/z 643 [M]⁺; IR (KBr): 2131 cm⁻¹, 2162 cm⁻¹; elemental analyses calcd for C₃₀H₂₄AuNO₃.½H₂O (found): C, 55.22 (55.42); H, 3.86 (3.82); N, 2.15 (2.19).

Compound 14 [Au(4-mpmepy)(C≡C—C₆H₄—OCH₃-p)₂] (4-mpmepy=4-methyl-2-(p-methoxyphenyl)pyridine) Yield: 26%. ¹H NMR (300 MHz, CD₂Cl₂, 298 K, relative to Me₄Si): δ 2.50 (s, 3H, —CH₃), 3.80 (s, 6H, —OCH₃), 3.86 (s, 3H, —OCH₃), 6.85 (m, 5H, phenyl and 4-mpmepy), 7.12 (d, 6.1 Hz, 1H, 4-mpmepy), 7.46 (m, 4H, phenyl), 7.56 (s, 1H, 4-mpmepy), 7.64 (d, 8.7 Hz, 1H, 4-mpmepy), 7.82 (d, 2.7 Hz, 1H, 4-mpmepy), 9.35 (d, 6.1 Hz, 1H, 4-mpmepy); positive FAB-MS: m/z 658 [M]⁺; IR (KBr): 2129 cm⁻¹, 2160 cm⁻¹; elemental analyses calcd for C₃₀H₂₄NO₂Au.½H₂O (found): C, 56.61 (56.26); H, 3.96 (4.09); N, 2.20 (2.22).

Compound 15 [Au(mptfpy)(C≡C—C₆H₄—OCH₃-p)₂] (mptfpy=5-trifluoromethyl-2-(p-methoxyphenyl)pyridine) Yield: 22%. ¹H NMR (300 MHz, CD₂Cl₂, 298 K, relative to Me₄Si): δ 3.80 (s, 6H, —OCH₃), 3.88 (s, 3H, —OCH₃), 6.84-6.91 (m, 5H, phenyl and mptfpy), 7.43-7.50 (m, 4H, phenyl), 7.75 (d, 8.5 Hz, 1H, mptfpy), 7.82 (d, 2.6 Hz, 1H, mptfpy), 7.90 (d, 7.9 Hz, 1H, mptfpy), 8.17 (d, 8.5 Hz, 1H, mptfpy), 9.96 (s, 1H, mptfpy); positive FAB-MS: m/z 712 [M]⁺; IR (KBr): 2138 cm⁻¹, 2161 cm⁻¹; elemental analyses calcd for C₃₁H₂₃NO₃F₃Au.½CH₂Cl₂ (found): C, 50.18 (50.35); H, 3.21 (3.14); N, 1.86 (1.97).

Compound 16 [Au(ppy)(C≡C—Si(CH₃)₃)₂] (ppy=2-phenylpyridine) Yield: 12%. ¹H NMR (400 MHz, CD₂Cl₂, 298 K, relative to Me₄Si): δ 0.23 (s, 9H, —Si(CH₃)₃), 0.25 (s, 9H, —Si(CH₃)₃), 7.31-7.43 (m, 3H, ppy), 7.69 (dd, 1.4 and 7.5 Hz, 1H, ppy), 7.91 (d, 8.1 Hz, 1H, ppy), 8.06 (m, 1H, ppy), 8.13 (dd, 1.4 and 7.5 Hz, 1H, ppy), 9.58 (d, 5.7 Hz, 1H, ppy); positive FAB-MS: m/z 546 [M]⁺; IR (KBr): 2075 cm⁻¹, 2098 cm⁻¹; elemental analyses calcd for C₂₁H₂₆NSi₂Au.½H₂O (found): C, 45.48 (45.12); H, 4.71 (4.91); N, 2.67 (2.53).

Compound 17 [Au(ptpy)(C≡C—Si(CH₃)₃)₂] (ptpy=2-(p-tolyl)pyridine) Yield: 15%. ¹H NMR (400 MHz, CD₂Cl₂, 298 K, relative to Me₄Si): δ 0.23 (s, 9H, —Si(CH₃)₃), 0.27 (s, 9H, —Si(CH₃)₃), 2.37 (s, 3H, —CH₃), 7.14 (d, 7.9 Hz, 1H, ppy), 7.35 (t, 6.1 Hz, 1H, ppy), 7.57 (d, 7.9 Hz, 1H, ppy), 7.84 (d, 7.9 Hz, 1H, ppy), 7.97 (s, 1H, ppy), 8.02 (m, 1H, ppy), 9.54 (d, 4.9 Hz, 1H, ppy); positive FAB-MS: m/z 560 [M]⁺; IR (KBr): 2075 cm⁻¹, 2098 cm⁻¹; elemental analyses calcd for C₂₂H₂₈NSi₂Au.½H₂O (found): C, 46.47 (46.50); H, 5.14 (5.07); N, 2.46 (2.46).

Compound 18 [Au(ppy)(C≡C—H)₂] (ppy=2-phenylpyridine) Yield: 48%. ¹H NMR (300 MHz, CD₂Cl₂, 298 K, relative to Me₄Si): δ 2.44 (s, 1H, —C≡C—H), 2.78 (s, 1H, —C≡C—H), 7.36-7.49 (m, 3H, ppy), 7.72 (d, 7.0 Hz, 1H, ppy), 7.94 (d, 8.1 Hz, 1H, ppy), 8.11 (m, 1H, ppy), 8.17 (dd, 2.0 and 6.5 Hz, 1H, ppy), 9.62 (6.5 Hz, 1H, ppy).

Compound 19 [Au(ppy)(tda)] (ppy=2-phenylpyridine; tda=tolan-2,2'-diacetylide) Yield: 39%. $^1$H NMR (400 MHz, DMSO-d$_6$, 298 K, relative to Me$_4$Si): δ 7.40-7.50 (m, 6H, phenyl), 7.65-7.68 (m, 2H, phenyl), 7.70-7.73 (m, 2H, ppy), 7.77 (t, 7.4 Hz, 1H, ppy), 8.07 (d, 7.5 Hz, 1H, ppy), 8.20 (dd, 1.3 and 7.9 Hz, 1H ppy), 8.35-8.43 (m, 2H, ppy), 9.50 (d, 6.2 Hz, 1H, ppy); positive-ion FAB MS: m/z 576 [M+1]$^+$; elemental analysis calcd for C$_{29}$H$_{16}$AuN.1½H$_2$O (found): C, 57.82 (57.89); H, 2.94 (3.18); N, 2.33 (2.43).

Compound 20 [Au(piq)(C≡C—C$_6$H$_4$—OCH$_3$)$_2$] (piq=1-phenylisoquinoline) Yield: 36%. $^1$H NMR (300 MHz, CD$_2$Cl$_2$, 298 K, relative to Me$_4$Si): δ 3.80 (s, 6H, —OCH$_3$), 6.85 (m, 4H, phenyl), 7.45 (m, 6H, phenyl and piq), 7.77 (d, 6.4 Hz, 1H, piq), 7.84 (d, 8.5 Hz, 1H, piq), 7.91 (t, 6.5 Hz, 1H, piq), 8.00 (d, 8.5 Hz, 1H, piq), 8.24 (d, 7.2 Hz, 1H, piq), 8.39 (dd, 2.1 and 7.2 Hz, 1H, piq), 8.90 (d, 8.5 Hz, 1H, piq), 9.59 (d, 6.4 Hz, 1H, piq); positive FAB-MS: m/z 664 [M]$^+$; IR (KBr): 2129 cm$^{-1}$, 2160 cm$^{-1}$; elemental analyses calcd for C$_{33}$H$_{24}$NO$_2$Au.CH$_2$Cl$_2$ (found): C, 54.56 (54.99); H, 3.50 (3.54); N, 1.87 (2.27).

Compound 21 [Au(mpiq)(C≡C—C$_6$H$_4$—OCH$_3$)$_2$] (mpiq=1-(p-methoxyphenyl)isoquinoline) Yield: 56%. $^1$H NMR (400 MHz, CD$_2$Cl$_2$, 298 K, relative to Me$_4$Si): δ 3.81 (s, 6H, —OCH$_3$), 3.92 (s, 3H, —OCH$_3$), 6.85 (m, 4H, phenyl), 6.92 (dd, 2.8 and 8.8 Hz, 1H, mpiq), 7.48 (m, 4H, phenyl), 7.64 (d, 6.8 Hz, 1H, mpiq), 7.78 (t, 6.8 Hz, 1H, mpiq), 7.88 (t, 6.8 Hz, 1H, mpiq), 7.94 (d, 7.8 Hz, 1H, mpiq), 8.01 (d, 2.8 Hz, 1H, mpiq), 8.20 (d, 9.0 Hz, 1H, mpiq), 8.82 (d, 8.8 Hz, 1H, mpiq), 9.48 (d, 6.8 Hz, 1H, mpiq); positive FAB-MS: m/z 694 [M]$^+$; IR (KBr): 2129 cm$^{-1}$, 2162 cm$^{-1}$; elemental analyses calcd for C$_{34}$H$_{26}$AuNO$_3$.½H$_2$O (found): C, 58.13 (58.17); H, 3.87 (3.80); N, 1.99 (1.98).

Compound 22 [Au(bzq)(C≡C—C$_6$H$_4$—OCH$_3$)$_2$] (bzq=7,8-benzoquinoline) Yield: 56%. $^1$H NMR (300 MHz, CD$_2$Cl$_2$, 298 K, relative to Me$_4$Si): δ 3.81 (s, 6H, —OCH$_3$), 6.88 (m, 4H, phenyl), 7.53 (m, 4H, phenyl), 7.76 (m, 3H, bzq), 7.85 (d, 8.1 Hz, 1H, bzq), 7.92 (d, 8.1 Hz, 1H, bzq), 8.38 (d, 7.1 Hz, 1H, bzq), 8.56 (d, 8.1 Hz, 1H, bzq), 9.82 (d, 5.3 Hz, 1H, bzq); positive FAB-MS: m/z 694 [M]$^+$; IR (KBr): 2127 cm$^{-1}$, 2160 cm$^{-1}$; elemental analyses calcd for C$_{31}$H$_{22}$AuNO$_2$.H$_2$O (found): C, 56.80 (56.88); H, 3.69 (3.46); N, 2.14 (2.20).

UV-Vis Absorption Properties

Figure 1:
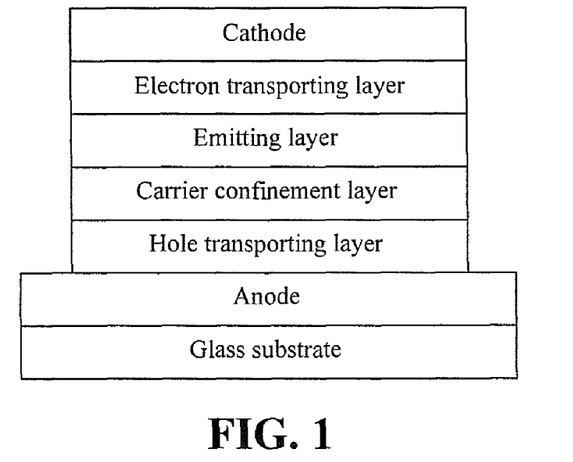
FIG. 1 is a schematic diagram of an organic EL device according to an embodiment of the invention.
Figure 2:
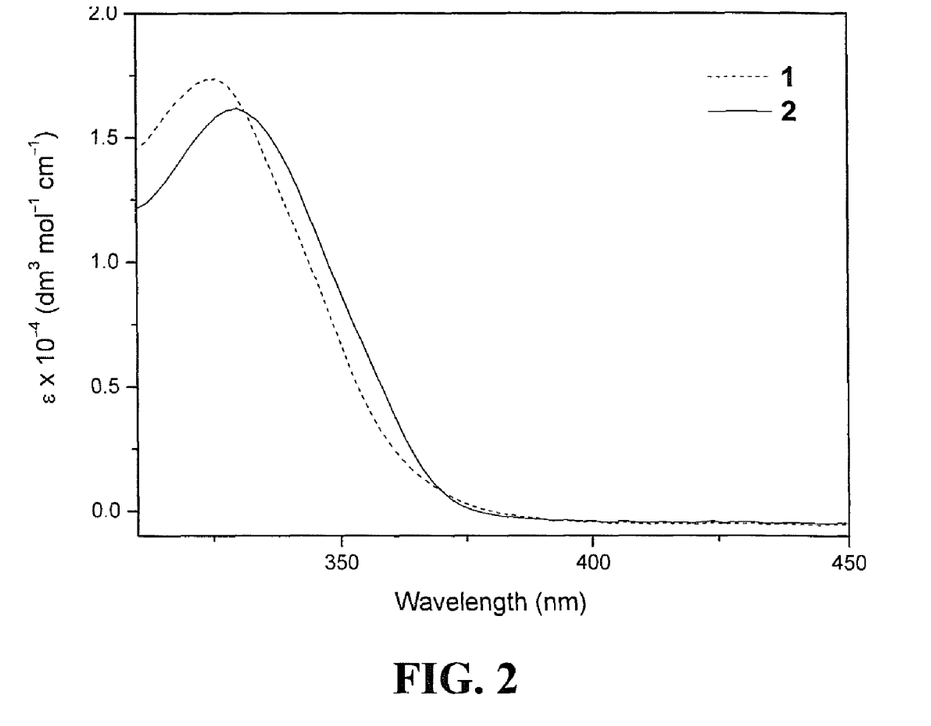
FIG. 2 shows UV-vis absorption spectra of compounds 1 and 2 in dichloromethane at 298 K.

Gold(III) compounds according to the invention exhibit rich luminescence at temperature up to normal room in various media. The photophysical data of selected compounds are summarized in Table 1. The UV-vis absorption spectra of compounds 1 and 2 are shown in FIG. 2 as representative examples, in which compounds 1 and 2 show only one intense structureless band at ca. 326 nm and 330 nm respectively in dichloromethane solution at 298 K. The origin of the absorption at 326-330 nm is tentatively assigned as the intraligand (IL) π-π* transition of the bidentate C^N ligand. Compound 1 shows a lower absorption energy than that of 2, presumably due to the electron-donating methyl group on the phenyl ring of the C^N ligand narrowing the HOMO-LUMO energy gap for the transition by raising the energy of the HOMO π orbital to a higher extent compared to the LUMO π* orbital.

Photoluminescence Properties

Figure 3:
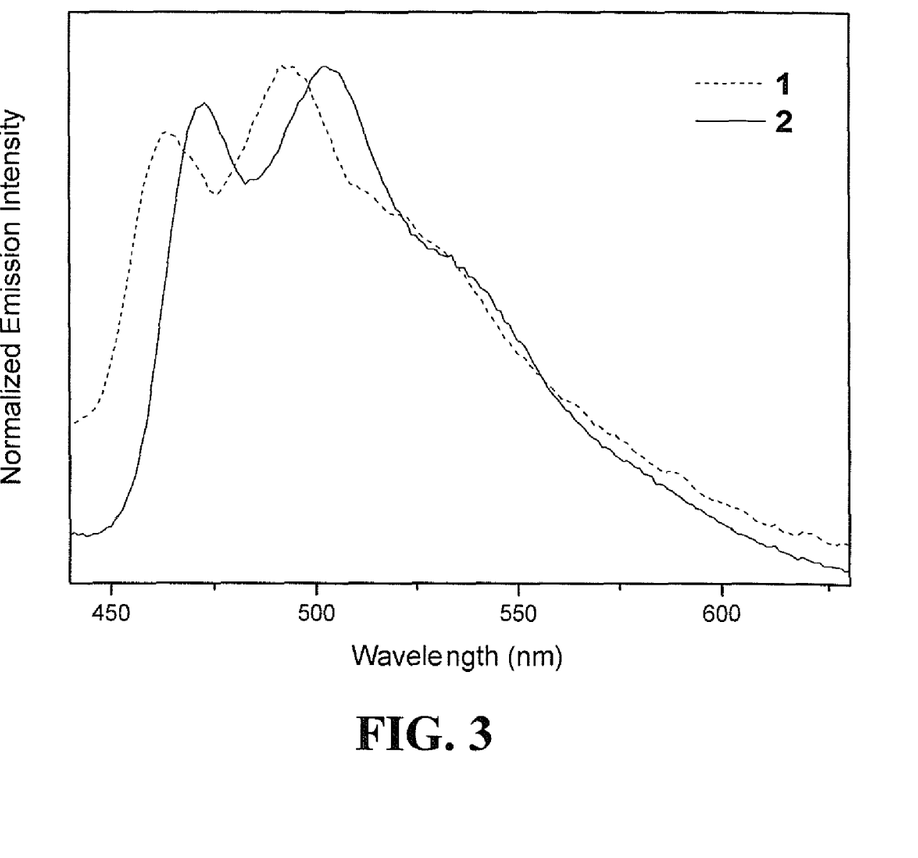
FIG. 3 shows emission spectra of compounds 1 and 2 in dichloromethane at 298 K where no instrumental correction was applied for the emission wavelength.

Unlike most other Au(III) compounds which are non-emissive or only show luminescence at low temperature, this class of compounds displays intense luminescence at 462-697 nm in the solution state at room temperature (Table 1). As illustrated in the representative emission spectra in FIG. 3, compounds 1 and 2 exhibit intense vibronic-structured emission bands at 460-505 nm. The vibrational progressional spacings are in the range of 1225-1260 cm$^{-1}$, corresponding to C=C and C=N stretching frequencies, which suggests the assignment of the vibronic-structured bands as originated from metal-perturbed intraligand $^3$[π-π*] state of the C^N ligand. Compound 2 exhibits a red shift in the emission compared to compound 1, which is consistent with the electronic absorption study, and is presumably due to the electron-donating methyl substituent on the C^N ligand reducing the HOMO-LUMO energy gap for the π-π* transition.

TABLE 1

Photophysical data for selected compounds

| Compound | Medium (T/K) | Absorption λ$_{max}$/nm (ε$_{max}$/dm$^3$mol$^{-1}$cm$^{-1}$) | Emission λ$_{max}$/nm |
|---|---|---|---|
| 1 | CH$_2$Cl$_2$ (298) | 326 (17365) | 464, 492, 524sh |
| 2 | CH$_2$Cl$_2$ (298) | 330 (16175) | 473, 503, 540sh |
| 4 | CH$_2$Cl$_2$ (298) | 324 (20575) | 472, 502, 534sh |
| 5 | CH$_2$Cl$_2$ (298) | 320 (16905) | 462, 493, 524sh |
| 6 | CH$_2$Cl$_2$ (298) | 330sh (9685) | 464, 493, 522sh |
| 7 | CH$_2$Cl$_2$ (298) | 330sh (16265) | 491, 520, 556sh |
| 8 | CH$_2$Cl$_2$ (298) | 330 (21650) | 470, 500, 532sh |
| 9 | CH$_2$Cl$_2$ (298) | 332sh (19260) | 592 |
| 13 | CH$_2$Cl$_2$ (298) | 330 (15820) | 487, 514, 553sh |
| 14 | CH$_2$Cl$_2$ (298) | 326sh (15530) | 479, 507, 549sh |
| 20 | CH$_2$Cl$_2$ (298) | 362 (13565) | 582, 621 |
| 21 | CH$_2$Cl$_2$ (298) | 398 (27835) | 592, 632, 697sh |

EXAMPLE 2

Photoluminescence (PL) properties of luminescent gold (III) compounds in solid thin film were studied by doping 20 wt % compound 2 into a high triplet energy host matrix, formed by mixing 70 wt % poly(N-vinyl-carbazole) (PVK) with 30 wt % 2-(4-butylphenyl)-5-(4-tert-biphenylyl)-1,3,4-oxadiazole (butyl-PBD). The dye-doped PVK:butyl-PBD blend was spin-coated onto a quartz substrate from a 28 mg/ml solution (total solids) in 1,2-dichloroethane (DCE) at 3000 rpm for 30 seconds to form 70 nm thin film. PL spectrum was obtained on a Spex Fluorolog-2 model F-111 fluorescence spectrofluorometer equipped with a Hamamatsu R-928 photomultiplier tube.

EXAMPLE 3

Figure 4:
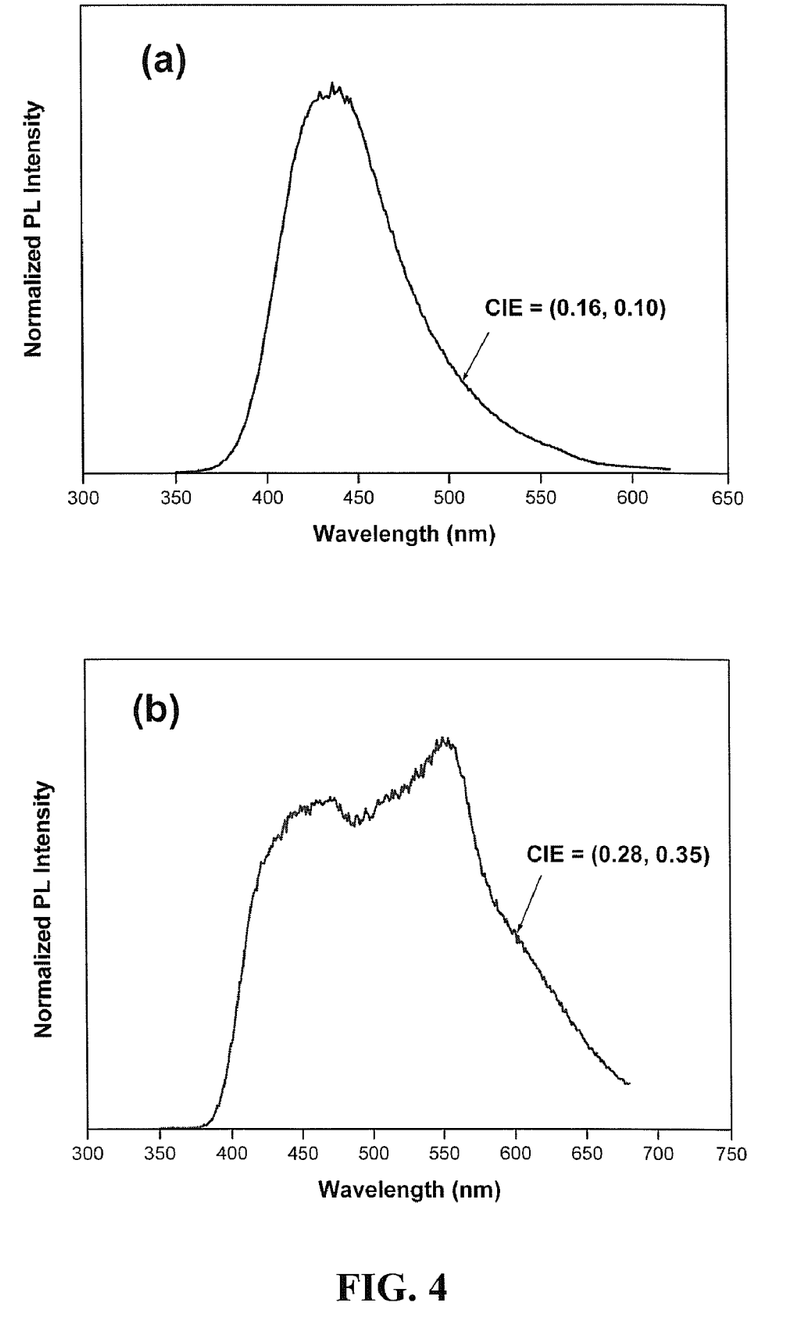
FIG. 4 shows solid state emission spectra of undoped PVK:butyl-PBD and compound 2 doped PVK:butyl-PBD thin films.

The same materials and processing procedures were employed as described in Example 2, except that a purely undoped 70 wt % PVK:30 wt % butyl-PBD was used instead of the dye-doped thin film. FIG. 4 shows a photoluminescence spectra of dye-doped and undoped PVK:butyl-PBD thin films. As shown in FIG. 4(a), the undoped PVK:butyl-PBD thin film exhibits intense deep blue emission with a dominating peak at 437 nm, corresponding to Commission Internationale de l'éclairage (CIE) coordinates of (0.16, 0.10). The dye-doped thin film shows an additional peak at 554 nm, which is expected to be arising from compound 2, as shown in FIG. 4(b). In particular, a white emission with CIE of (0.28, 0.35) was obtained when compound 2 was doped into the PVK:butyl-PBD matrix.

EXAMPLE 4

An OLED device according to an embodiment of the invention was constructed in the following manner
a) a transparent anode ITO-coated glass substrate was cleaned ultrasonically in a commercial detergent, rinsed in deionized water, and then dried in an oven. The substrate was subsequently subjected to an UV-ozone treatment for 15 minutes;
b) the substrate was put into a vacuum chamber, and the chamber was pumped down to 5×10⁻⁶ mbar;
c) a 70 nm thick N,N'-di(1-naphthyl)-N,N'-diphenylbenzidine (NPB) hole-transporting layer was deposited on ITO-coated glass substrate;
d) a 5 nm thick CBP carrier confinement layer was deposited on NPB layer;
e) a 30 nm thick doped CBP light-emitting layer was deposited on CBP layer, in which 2, 4, 6, 8, and 10% v/v compound 1 was doped into light-emitting CBP layer;
f) a 30 nm thick aluminum(III) bis(2-methyl-8-quinolinato)-4-phenylphenolate (BAlq) electron-transporting layer was deposited on doped CBP light-emitting layer;
g) a 0.5 nm thick LiF and a 200 nm thick Al were deposited on the BAlq layer as electron-injecting cathode.

All materials were prepared by thermal evaporation from tantalum boats. Deposition rates were monitored with a quartz oscillation crystal and controlled at 0.1-0.2 nm/s for both organic and metal layers. J-V-L characteristics of OLED devices were measured with a programmable Keithley model 2420 power source and a Spectrascan PR655 colorimeter under ambient air conditions.

Figure 5:
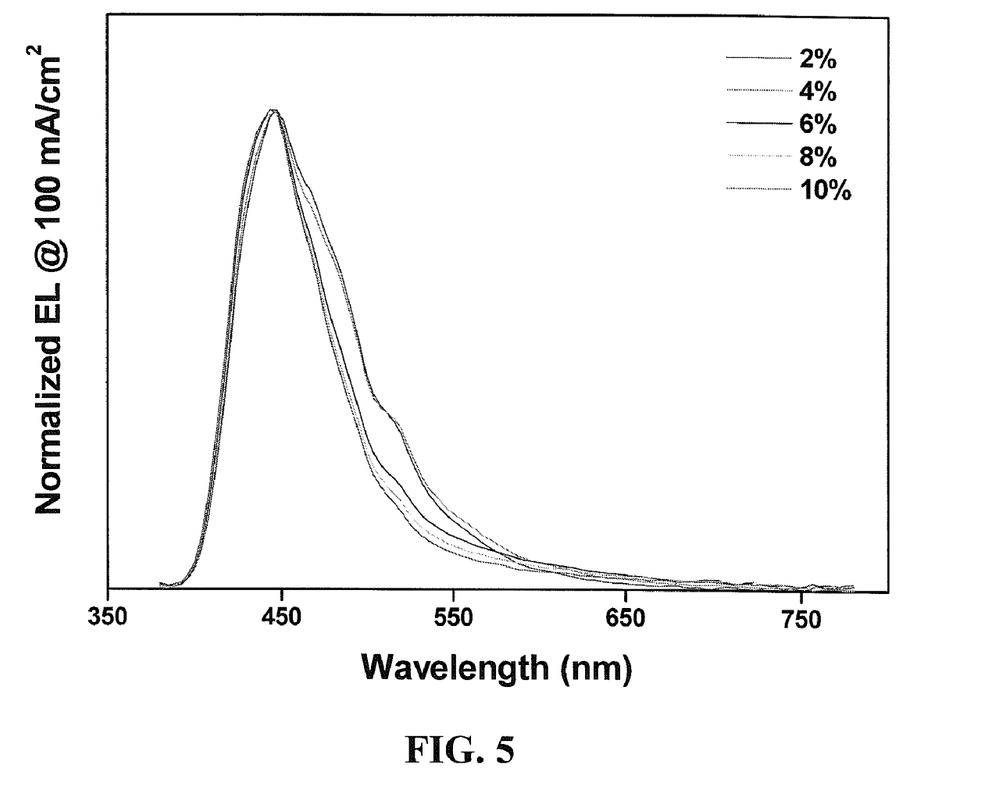
FIG. 5 shows the EL spectra for devices of Example 4 where the spectral lines for increasing concentration of compound 1 (2% through 10%) display decreasing absorption at 484 and 518 nm.

FIG. 5 depicts the EL spectra for devices of Example 4, in which the concentration of compound 1 doped into a CBP host material varies from 2 to 10%. Remarkably, all devices show broad EL spectra with emission peaks at ca. 448, 485, and 518 nm. With increasing the concentration of compound 1, the relative intensities of 484 and 518 nm drops. This corresponds to a color change in CIE coordinates from (0.17, 0.16) to (0.17, 0.11) and a decrease in the full width at half maximum from 76 nm (3688 cm⁻¹) to 63 nm (3119 cm⁻¹) as the concentration of compound 1 increases from 2 to 10%. This demonstrates that the luminescent gold(III) compounds according to embodiments of the present invention can be effectively used as phosphorescent dopants for the fabrication of OLEDs.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:
1. A luminescent gold(III) compound having the chemical structure:

(I)

wherein:
X is nitrogen and Y is carbon or nitrogen;
A-B is a substituted or unsubstituted cyclometalating ligand (for Y=C) or diimine ligand (for Y=N);
wherein A and B are cyclic structure derivatives, and the ring A and the ring B can be fused together or the ring A and the ring B can be non-fused;
wherein when the ring A and the ring B are fused together, A is selected from substituted or unsubstituted pyridine or isoquinoline; and B is selected from substituted or unsubstituted benzene, pyridine, isoquinoline, anthracene, pyrene, carbazole, or fluorene;
wherein when the ring A and the ring B are not fused together, A is selected from substituted or unsubstituted pyridine or isoquinoline; and B is selected from substituted or unsubstituted benzene, pyridine, isoquinoline, naphthalene, anthracene, pyrene, carbazole, or fluorene;
wherein the rings A and B are unsubstituted or wherein one or both of the rings A and B have at least one substituent comprising alkyl, alkenyl, alkynyl, alkylaryl, cycloalkyl, OR, NR₂, SR, C(O)R, C(O)OR, C(O)NR₂, CN, CF₃, NO₂, SO₂, SOR, SO₃R, halo, aryl, substituted aryl, heteroaryl, substituted heteroaryl or heterocyclic group, wherein R is independently alkyl, alkenyl, alkynyl, alkylaryl, aryl, or cycloalkyl;
R₁ and R₂ are independently optionally substituted carbon donor ligands selected from alkynyl, substituted alkynyl, arylalkynyl, or substituted arylalkynyl; and
n is greater than or equal to zero.

2. The gold(III) compound of claim 1, wherein at least one of rings A and B independently has adjacent positions that in combination form a fused 5- to 6-member cyclic group, wherein the cyclic group is cycloalkyl, cycloheteroalkyl, aryl, or heteroaryl, and wherein the fused 5- to 6-member cyclic group is optionally substituted with one or more alkyl, alkenyl, alkynyl, alkylaryl, cycloalkyl, CN, CF₃, C(O)OR, C(O)R, NR₂, NO₂, OR, or halo substituent where R is independently alkyl, alkenyl, alkynyl, alkylaryl, aryl or cycloalkyl.

3. The gold(III) compound of claim 1, wherein the cyclometalating ligand A-B comprises 2-phenylpyridines, phenylisoquinolines, or any derivative thereof wherein the derivative is substituted with at least one alkyl, alkenyl, alkynyl, alkylaryl, cycloalkyl, OR, NR₂, SR, C(O)R, C(O)OR, C(O)NR₂, CN, CF₃, NO₂, SO₂, SOR, SO₃R, halo, aryl, substituted aryl, heteroaryl, substituted heteroaryl or a heterocyclic group, and wherein, optionally, any two adjacent substituted positions of the rings A and/or B in combination form, independently, a fused 5- to 6-member cyclic group, wherein the cyclic group is cycloalkyl, cycloheteroalkyl, aryl, or heteroaryl, and wherein the fused 5- to 6-member cyclic group is optionally substituted with one or more alkyl, alkenyl, alkynyl, alkylaryl, cycloalkyl, OR, C(O)R, C(O)OR, C(O)NR₂, CN, CF₃, NR₂, NO₂, SR, SO₂, SOR, SO₃R, or halo, wherein R is independently alkyl, alkenyl, alkynyl, alkylaryl, aryl or cycloalkyl; or wherein the diimine ligand A-B comprises 2,2'-bipyridines, 1,10-phenanthrolines, or a derivative thereof, wherein the derivative is substituted with one or more alkyl, alkenyl, alkynyl, alkylaryl, cycloalkyl, OR, NR₂, SR, C(O)R, C(O)OR, C(O)NR₂, CN, CF₃, NO₂, SO₂, SOR, SO₃R, halo, aryl, substituted aryl, heteroaryl, substituted heteroaryl or heterocyclic group, and wherein, optionally, any two adjacent substituted positions of the rings A and/or B in combination form, independently, a fused 5- to 6-member cyclic group, wherein the cyclic group is cycloalkyl, cycloheteroalkyl, aryl, or heteroaryl, and wherein the fused 5- to 6-member cyclic group is optionally substituted with one or more alkyl, alkenyl, alkynyl, alkylaryl, cycloalkyl, OR, C(O)

R, C(O)OR, C(O)NR$_2$, CN, CF$_3$, NR$_2$, NO$_2$, SR, SO$_2$, SOR, SO$_3$R, or halo, wherein R is independently alkyl, alkenyl, alkynyl, alkylaryl, aryl or cycloalkyl.

4. The gold(III) compound of claim 1, wherein the gold(III) compound has photoluminescence properties and/or electroluminescence properties.

5. The gold(III) compound of claim 1, wherein the gold(III) compound is Au(2-phenylpyridine)(C≡C—C$_6$H$_4$—OCH$_3$-p)$_2$, Au(2-(p-tolyl)pyridine)(C≡C—C$_6$H$_4$—OCH$_3$-p)$_2$, Au(2,2'-bipyridine)(C≡C—C$_6$H$_4$—OCH$_3$-p)$_2$, Au(2-(p-tolyl)pyridine)(C≡C—C$_6$H$_4$—C$_4$H$_9$-p)$_2$, Au(2-phenylpyridine)(C≡C—C$_6$H$_4$—C$_2$H$_5$-p)$_2$, Au(2-phenylpyridine)(C≡C—C$_6$H$_4$—CF$_3$-p)$_2$, Au(5-methyl-2-p-(methoxyphenyl)pyridine)(C≡C—C$_6$H$_4$—OCH$_3$-p)$_2$, Au(2-(p-(tert-butyl)phenyl)pyridine (C≡C—C$_6$H$_4$—OCH$_3$-p)$_2$, Au(2-phenylpyridine)(C≡C—C$_6$H$_4$—NH$_2$-p)$_2$, Au(2-(p-tolyl)pyridine)(C≡C—C$_6$H$_4$—NH$_{2-p}$)$_2$, Au(2-phenylpyridine)(C≡C—C$_6$H$_4$—N(CH$_3$)$_2$-p)$_2$, Au(2-(p-tolyl)pyridine)(C≡C—C$_6$H$_4$—N(CH$_3$)$_2$-p)$_2$, Au(2-(p-methoxyphenyl)pyridine)(C≡C—C$_6$H$_4$—OCH$_3$-p)$_2$, Au(4-methyl-2-(p-methoxyphenyl)pyridine)(C≡C—C$_6$H$_4$—OCH$_3$-p)$_2$, Au(5-trifluoromethyl-2-(p-methoxyphenyl)pyridine)(C≡C—C$_6$H$_4$—OCH$_3$-p)$_2$, Au(2-phenylpyridine)(C≡C—Si(CH$_3$)$_3$)$_2$, Au(2-(p-tolyl)pyridine)(C≡C—Si(CH$_3$)$_3$)$_2$, Au(2-phenylpyridine)(C≡C—H)$_2$, Au(2-phenylpyridine)(tolan-2,2'-diacetylide), Au(1-phenylisoquinoline)(C≡C—C$_6$H$_4$—OCH$_3$-p)$_2$, or Au(1-(p-methoxyphenyl)isoquinoline)(C≡C—C$_6$H$_4$—OCH$_3$-p)$_2$.

6. A light-emitting device comprising a layer comprising the gold(III) compound of claim 1 wherein the layer emits light.

7. The light-emitting device of claim 6, wherein the device has a layer structure comprising a cathode layer, an electron-transporting layer, the layer comprising the gold(III) compound, a carrier confinement layer, a hole-transporting layer, and an anode layer.

8. A method of preparation of luminescent gold(III) compounds according to claim 1, comprising:
providing a gold(III) dichloride complexed with a cyclometalating ligand or diimine ligand; and
reacting the complexed gold(III) dichloride with a strong σ-donating ligand precursor, wherein the luminescent gold(III) compound according to claim 1 is formed.

9. The method of claim 8, wherein the diimine ligand is 2,2'-bipyridine or the cyclometalating ligand is 2-phenylpyridine, 2-(p-tolyl)pyridine, 5-methyl-2-(p-methoxyphenyl)pyridine, 2-(p-(tert-butyl)phenyl)pyridine, 2-(p-methoxyphenyl)pyridine, 4-methyl-2-(p-methoxyphenyl)pyridine, 5-trifluoromethyl-2-(p-methoxyphenyl)pyridine, 1-phenylisoquinoline, or 1-(p-methoxyphenyl)isoquinoline.

10. The method of claim 8, wherein the strong σ-donating ligand precursor comprises an alkynyl metal, arylalkynyl metal, substituted alkynyl metal or substituted arylalkynyl metal.

11. The method of claim 10, wherein: the substituted arylalkynyl metal comprises LiC≡C—C$_6$H$_4$—OCH$_3$-p, LiC≡C—C$_6$H$_4$—C$_4$H$_9$-p, LiC≡C—C$_6$H$_4$—C$_2$H$_5$-p, LiC≡C—C$_6$H$_4$—CF$_3$-p, LiC≡C—C$_6$H$_4$—NH$_2$-p, LiC≡C—C$_6$H$_4$—N(CH$_3$)$_2$-p, or LiC≡C—C$_6$H$_4$—C≡C—C$_6$H$_4$—C≡CLi; or the substituted alkynyl metal comprises LiC≡C—Si(CH$_3$)$_3$.

12. The method of claim 8, wherein reacting occurs in solution.

13. The method of claim 8, further comprising purifying the luminescent gold(III) compound by chromatography, sublimation, crystallization, extraction, or any combination thereof.

14. A method of preparation of luminescent gold(III) compounds according to claim 1, comprising:
providing a luminescent gold(III) compound where in A-B is a substituted or unsubstituted cyclometalating ligand (for Y═C) or diimine ligand (for Y═N), wherein R$_1$ and/or R$_2$ are independently substituted alkynyl wherein the substituent acts as a protecting group; and
deprotecting the luminescent gold(III) compound with a deprotecting agent,
wherein the luminescent gold(III) compound according to claim 1 is formed.

15. The method of claim 14, wherein the cyclometalating ligand is 2-phenylpyridine.

16. The method of claim 14, wherein the protected luminescent gold(III) compound is [Au(2-phenylpyridine)(C≡C—Si(CH$_3$)$_3$)$_2$] and wherein the deprotecting agent is tetra-n-butylammonium fluoride (TBAF).

* * * * *

UNITED STATES PATENT AND TRADEMARK OFFICE
CERTIFICATE OF CORRECTION

PATENT NO. : 8,372,977 B2
APPLICATION NO. : 12/822812
DATED : February 12, 2013
INVENTOR(S) : Vivian Wing-Wah Yam et al.

It is certified that error appears in the above-identified patent and that said Letters Patent is hereby corrected as shown below:

Title Page,
(57) Abstract, Line 2, "compounds contains" should read --compounds containing--.

In the Specification:

Column 5,
Line 18, "6-donating" should read --σ-donating--.

Column 6,
Line 43, "alkyl groups" should read --alkyl group--.

Column 7,
Lines 31-32, "5- or 6-membered rings." should read --5- or 6-membered ring.--.

Column 8,
Line 17, "4,7-bis(4-bromophenyl)-1,10-phenanthro line" should read --4,7-bis(4-bromophenyl)-1,10-phenanthroline --.
Lines 18-19, "5,6-dimethyl-1,10-phenanthro line" should read --5,6-dimethyl-1,10-phenanthroline --.
Line 26, "5-carboxy-1,10-phenanthro line" should read --5-carboxy-1,10-phenanthroline--.

Column 9,
Line 49, "used those that" should read --used in those that--.

Column 12,
Line 53, "(s, 6H, -CH$_3$)," should read --(s, 6H, -OCH$_3$),--.

Signed and Sealed this
Twenty-fourth Day of September, 2013

Teresa Stanek Rea
*Deputy Director of the United States Patent and Trademark Office*

CERTIFICATE OF CORRECTION (continued)
U.S. Pat. No. 8,372,977 B2

In the Claims:

Column 19, Claim 5
Line 9, "Au(2-(p-tolyl)pyridine)(C=C-$C_6H_4$-$OCH_3$-p)$_2$" should read --Au(2-($p$-tolyl)pyridine)(C≡C-$C_6H_4$-$OCH_3$-$p$)$_2$--.
Line 25, "Au(2-phenylpyridine)(C-H)$_2$" should read --Au(2-phenylpyridine)(C≡C-H)$_2$--.

Column 20, Claim 11
Lines 16-17, "LiC≡C-$C_6H_4$-C=C-$C_6H_4$-C≡CLi" should read --LiC≡C-$C_6H_4$-C≡C-$C_6H_4$-C≡CLi--.